United States Patent [19]

Tsukahara et al.

[11] Patent Number: 4,876,070

[45] Date of Patent: Oct. 24, 1989

[54] AIR BLOWER APPARATUS

[75] Inventors: Hitoshi Tsukahara; Keiko Kurokawa; Toshimitsu Tsukui; Toshitake Nagai, all of Gunma, Japan

[73] Assignee: Sanyo Electric Co., Ltd., Osaka, Japan

[21] Appl. No.: 118,272

[22] Filed: Nov. 6, 1987

[30] Foreign Application Priority Data

Nov. 6, 1986 [JP] Japan .................... 61-264300

[51] Int. Cl.$^4$ .............................................. A62B 11/00
[52] U.S. Cl. ................................. 422/122; 55/279; 55/389; 210/501; 422/28; 422/124
[58] Field of Search ............... 422/28, 122, 124, 125; 55/528, 279, 472, 389; 210/501

[56] References Cited

U.S. PATENT DOCUMENTS

| | | | |
|---|---|---|---|
| 3,543,940 | 12/1970 | Schmidt | 210/501 X |
| 3,768,233 | 10/1973 | Mateson | 55/279 X |
| 3,862,030 | 1/1975 | Goldberg | 210/501 X |
| 4,142,030 | 2/1979 | Dieterich et al. | 521/122 X |
| 4,145,291 | 3/1979 | Console et al. | 210/501 X |
| 4,147,680 | 4/1979 | Reischl et al. | 521/163 X |
| 4,191,543 | 3/1980 | Peters | 55/279 |
| 4,534,775 | 8/1985 | Frazier | 422/122 X |
| 4,601,831 | 7/1986 | Cook | 210/501 X |
| 4,604,110 | 8/1986 | Frazier | 422/122 X |
| 4,631,297 | 12/1986 | Battice et al. | 422/122 X |
| 4,678,571 | 7/1987 | Hosaka et al. | 210/501 X |

FOREIGN PATENT DOCUMENTS

| | | |
|---|---|---|
| 0026061 | 7/1978 | Japan .................... 210/501 |
| 846458 | 8/1960 | United Kingdom . |
| 1346762 | 2/1974 | United Kingdom . |
| 2021435 | 12/1979 | United Kingdom . |

Primary Examiner—Robert J. Hill, Jr.
Assistant Examiner—Amalia L. Santiago
Attorney, Agent, or Firm—Darby & Darby

[57] ABSTRACT

Disclosed is an air blower apparatus for conditioning a room, including synthetic resin components which come in contact with air flow. The synthetic resin components are molded from polypropylene resin, to which at least one antimicrobial agent selected from diphenylethers, N-haloalkylthio compounds, benzimidazoles, organic arsine compounds and metal alumino-silicate hydrate is mixed prior to molding of the components.

17 Claims, 1 Drawing Sheet

AIR BLOWER APPARATUS

BACKGROUND OF THE INVENTION

1. Field of the Invention

This invention relates to an air blower apparatus for conditioning a room such as an air conditioner for cooling, heating and humidifying a room, an air circulator for circulating the air in a room or the like.

2. Description of the Prior Art

When a closed room is cooled or warmed with an air conditioner or is warmed and humidified at the same time with an air conditioner and an air circulator, fungi which grow on the air filter, discharge and suction grilles, fan or fan casing are blown into the room and can cause people in the room to be affected by diseases of the respiratory system such as asthma.

To solve this problem, it has been attempted to spray conventional antimicrobial agents on the air discharge port of the air conditioner as described in the Japanese Unexamined Utility Model Publication No. 7729/1986.

However, the application of an antimicrobial agent serves to prevent fungi growth but causes another problem that the antimicrobial agent may be easily removed by dewdrops which appear on the air discharge port of the air conditioner and therefore the antimicrobial effect cannot be maintained.

It is an object of the invention to provide an air blower apparatus which is free from such problem.

SUMMARY OF THE INVENTION

This invention provides an air blower apparatus having synthetic resin components for contact with the air flow. At least one antimicrobial agent selected from diphenylethers, N-haloalkylthio compounds, benzimidazoles, organic arsine compounds and metal alumino-silicate hydrate is added to the synthetic resin components.

PREFERRED EMBODIMENT OF THE INVENTION

Figure 1:
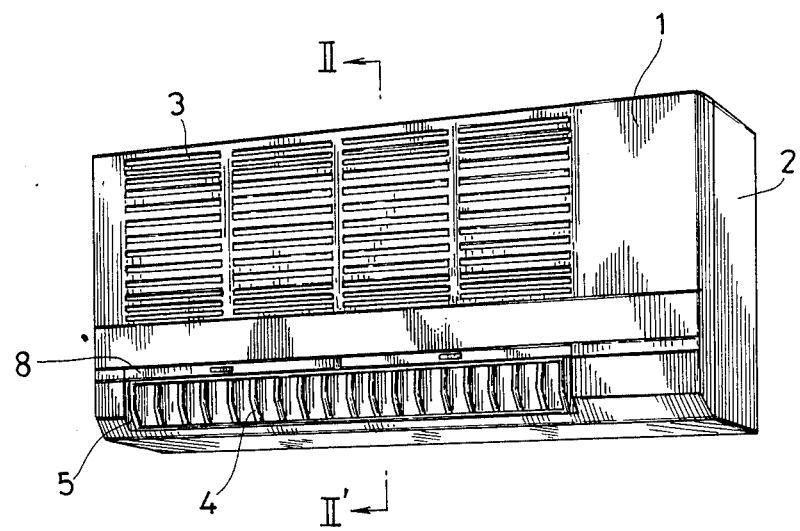
FIG. 1 is a perspective view of an air blower apparatus as one embodiment of this invention.

The wording "synthetic resin components for contact with the air flow" in this invention means the front panel, discharge and suction grill, body casing, fan casing, crossflow fan, air filter or other parts of the blower which are made of synthetic resins and contact the air flow. The preferred subject is the air filter net. The synthetic resins useful as the material of these components are not particularly limited. Specific examples include polypropylene resin (hereinafter described as PP resin), acrylonitrile-butadienestyrene resin (ABS resin), acrylonitrile-styrene resin (AS resin), polystyrene resin (PS resin) and the like.

The antimicrobial agents used for this invention are desirably those which are not easily decomposed at the molding temperature of the synthetic resin (approx. 200°–250° C.) and which possess antimicrobial effects against a variety of bacteria and fungi. We have found that the following five kinds of agents are preferable for meeting these criteria. Examples of the diphenylethers include 2,4,4'-trichloro-2'-hydroxydiphenylether ($C_{12}H_7Cl_3O_2$) and hexachlorohydroxydiphenylether ($C_{12}H_3Cl_6O_2$), examples of the N-haloalkylthio compounds include N-(fluorodichloromethylthio)-phthalimide ($C_9H_4Cl_2FNO_2S$), N,N-dimethyl-N'-phenyl-N'-fluorodichloromethylthiosulfamide ($C_6H_{12}Cl_2FN_2O_2S_2$) and N-trichloromethylthiotetrahydrophthalimide ($C_6H_8Cl_3NO_2S$). The benzimidazoles may be 2-(4-thiazolyl)benzimidazole ($C_{10}H_7N_3S$) and 2-(methoxycarbonylamino)benzimidazole ($C_9H_9N_3O_2$); the organic arsenic compounds may be 10,10'-oxybisphenoxyarsine ($C_{24}H_{16}As_2O_3$) and arsthinol ($C_{11}H_{14}AsNO_3S_2$); and the metal alumino-silicate hydrate is a salt represented by the formula $Me^2/n\ O\cdot Al_2O_3\cdot xSiO_2\cdot yH_2O$ (wherein $Me^2$ represents $Cu++$, $Ag++$ or $Zn++$; n, x and y represent natural numbers). These antimicrobial agents are available because all of them are well known. The antimicrobial agents may be used singly or in admixture thereof. We have found that the combination use of 2,4,4'-trichloro-2'-hydroxydiphenylether and N-(fluorodichloromethylthio)phthalimide is preferable.

The antimicrobial agent is used in an antimicrobially effective amount, generally in a concentration from 0.05 wt% to 4.0 wt% to the synthetic resin as the material of the component.

It is preferable to use the antimicrobial agent in the form of inclusion compound because this serves to prolong the antimicrobial effect. Materials which are used to prepare the inclusion compound of antimicrobial agent can be selected from those well known in the art. However, is is preferable that the above mentioned metal alumino-silicate hydrate as the antimicrobial agent be used as the material for preparing the inclusion compound of the four kinds of the antimicrobial agents mentioned, except this alumino-silicate. In such case, the metal alumino-silicate hydrate is used in an amount sufficient to enclose the antimicrobial agent, thereby forming a suitable inclusion compound.

The antimicrobial agent is normally mixed with the synthetic resin before molding the blower components. For example, pellets are firstly prepared from predetermined amounts of the antimicrobial agent and the synthetic resin, and then the resulting pellets together with synthetic resin pellets are heated up to a temperature of approx. 200°–250° C. to melt for forming by extruding. Methods for molding may be suitably selected according to the shape or kind of desired component.

The component can be composed of a separate inner resin layer and an outer resin layer, wherein (1) the antimicrobial agent is added only to the inner resin layer or (2) it is added at a lower concentration to the outer resin layer than to the inner resin layer. For example, 1.0–4.0 wt% could be included in the inner layer and 0.05–0.9 wt% in the outer layer. In case (1), the outer resin layer experiences no void due to the release of the antimicrobial agent and hence the antimicrobial agent contained in the inner resin layer does not disappear by release after a short period, but rather, exerts a prolonged effect during a semipermanent period. In case (2), even if all of the antimicrobial agent in the outer resin layer is released, the agent contained in the inner resin layer remains owing to its higher concentration and can maintain its effect.

The component having the double structure of the outer and inner resin layers may be formed for example by a double extruding method.

In addition, we have found that the addition of a coupling agent to the resin used for manufacturing the component is preferable. Examples of the coupling agents include silane coupling agents such as vinyltrichlorosilane ($CH_2=CH=Si-Cl_3$), vinyltriethoxysilane [$CH_2=CH-Si-(OC_2H_5)_3$], γ-glycidoxypropyltrimethoxysilane

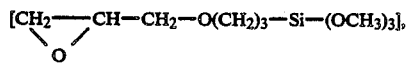

vinyl-tris-β-methoxyethoxysilane [$CH_2=CH-Si-(OC_2H_4OCH_3)_3$], N-β-(aminoethyl)-γ-aminopropyltrimethoxysilane[$NH_2-(CH_2)_2-NH-(CH_2)_3-Si-(OCH_3)_3$], and N-β-(aminoethyl)-γ-aminopropylmethyldimethoxysilane[$NH_2-(CH_2)_2-NH-(CH_2)_3-Si-(OCH_3)_3$]. Other coupling agents having a CHO radical such as glutaraldehyde [$CHO(CH_2)_3CHO$] are also usable.

The coupling agent to be used is selected according to the kind of resin. For example, N-β-(aminoethyl)-γ-aminopropylmethyldimethoxysilane is used for PP resin or ABS resin. The quantity of the coupling agent is 10–50 wt% of that of the antimicrobial agent.

The treatment of the coupling agent with the resin may be conducted by mixing the agennt and resin and extruding to make pellets. The resulting pellets can be mixed with the antimicrobial agent added-pellets to form the desired component as described above. This is an example of processing the coupling agent.

The use of the coupling agent can serve to strengthen the binding of the antimicrobial agent and the resin and prevent the antimicrobial agent from disappearing due to release over a short time.

In addition, it is preferable that the net of the air filter in the air blower apparatus according to this invention is made of PP resin woven or unwoven fabric. When the PP resin woven fabric is used for the net, it facilitates oil absorption due to the lipophilic nature as well as gaps between the threads interwoven each other. Therefore, the use of these fabrics for an air filter net of an air conditioner or circulating fan which is utilized in a kitchen or machine manufacturing factory serves to provide the circulation air without cooking oil or mist of processing oil. If the antimicrobial agent is coated on the air filter net of PP resin woven or unwoven fabric according to the methods of the prior art, it causes the drawbacks that the oil absorption is decreased, the adhesion of the antimicrobial agent to the PP resin fabric is weakened due to its being a crystalline resin and the antimicrobial agent is washed out during cleaning of the air filter net. However, this invention does not show such drawbacks, because the antimicrobial agent is included within the PP resin.

EXAMPLE

A specific example of the invention is explained as follows. In FIG. 1, 1 is a front panel installed in the front part of an air conditioner body 2 and equipped with a suction grille 3 and a discharge grille 5 with a louver 4.

Figure 2:
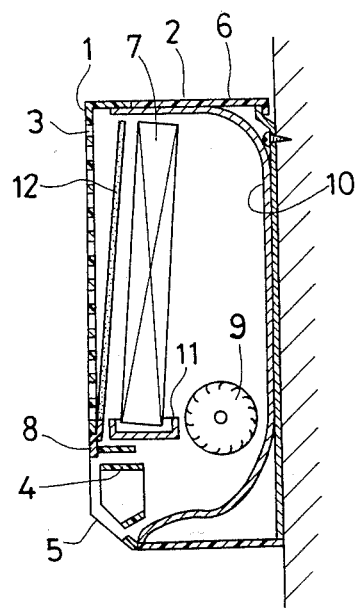
FIG. 2 is a cross-sectional view taken along the line II—II' of FIG. 1.
Figure 3:
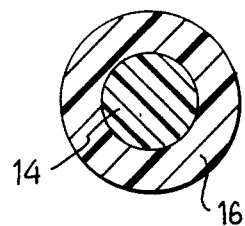
FIG. 3 is a cross-sectional view of the inner and outer layers of a filter of the invention.

In FIG. 2 which is a cross-sectional view taken along the line II-II' of FIG. 1, a casing 6 of the body 2 provides a heat exchanger 7 which acts as an evaporator when the air conditioner is used as a heater and also as a condenser when used as a cooler, a cross flow fan 9 to blow air drawn from the room through the suction grille 3, an air filter 8 and the heat exchanger 7 through the discharge grille 3, a fan casing 10 to guide the air from the suction grille 3 to the discharge grille 5, and a drain pan 11 to receive drained water which drops from the heat exchanger 7 when used as a cooler.

The casing 6, the front panel 1, the cross flow fan 9, the fan casing 10, and the louver 4 are molded a synthetic resin such as ABS resin, PP resin, PS resin or AS resin, to which 0.6–2.0 wt% of the antimicrobial agents of 2,4,4'-trichloro-2'-hydroxydiphenylether and N-(fluorodichloromethylthio)-phthalimide are added. Element 12 of the air filter 8 is made of woven fabric of PP resin to which is added 0.6–2.0 wt% of the same antimicrobial agent, and the drain pan 11 is made of a styrene foam to which is added with 0.6–2.0 wt% of the same agent.

Since the component to be in contact with the room air flow is made of the synthetic resin including the added antimicrobial agent, the existence of said agent in the surface and inner parts can prevent the occurrence or growth of fungi and bacteria at the discharge grille 5 and the lower fan 4 on which condensation appears in cooling; the drain pan 11 to receive drained water or the casing 6 the friont panel 1, the suction grille 3, the cross flow fan 9, the fan casing 10 and the net 12 of the air filter 9 which are moistened in heating and humidifying.

Next, the method for adding the antimicrobial agent into the air filter net and the antimicrobial effect of the net are explained as follows.

(Manufacture of the Net)

The antimicrobial agent [the combination of 2,4,4'-trichloro-2'-hydroxydiphenylether and N-(fluorodichloromethylthio)-phthalimide] was mixed with the PP resin so as to be in the ratio of 6–20 wt% and extruded to make pellets. The resulting pellets were mixed with PP resin pellets to obtain the specified mixing ratio of the antimicrobial agent (0.6–2.0 wt%), and subjected into an extruder (molding temperature: 200°–250° C.) to make threads, followed by knitting the threads to form a net. The net and a resin frame were integrally molded through an injection molder, to obtain the filter net.

A filter net without the addition of the antimicrobial agent was also manufactured for comparison.

(Antimicrobial Effect of the Net)

(1) An air conditioner for domestic use is usually equipped with two filter nets, one is installed at the left side of the blowing port and the other the right side thereof. In this test, the air conditioner was operated for a month under normal operating conditions, wherein one filter contained the antimicrobial agent and the other filter did not.

After the operation, the average number of microorganisms found per unit square ($8 \times 13$ cm.) of the net without the antimicrobial agent was $2.8 \times 10^2$, while that of the antimicrobial agent added net was $1.4 \times 10^2$. This result means a significant decrease of the number of micororganisms, because when the number found on microorganisms of the net without the antimicrobial agent is expressed as 100%, the decrease of the antimicrobial agent added-net is 50%.

(2) The above mentioned net with the antimicrobial agent was subjected to a Halo test.

In this test, fungi were cultivated in potato-dextrose agar medium at 25° C. for a week and bacteria were cultivated in agar medium added with yeast extract and glucose at 30° C. for three days. In cultivation, the antimicrobial agent added filter nets (27 mm. diam.)

were put on the medium and the width of growth inhibition zone (Halo) was measured.

The results were as follows.

| Test Strain | Result |
|---|---|
| Penicillium chrysogenum | +++ |
| | +++ |
| Fusarium oxysporum | ± |
| | ± |
| Pestalotia sp. | ++ |
| | ++ |
| Trichoderma viride | — |
| | — |
| Arthrinium sp. | ++ |
| | +++ |
| Staphylococcus aureus | +++ |
| | +++ |
| Bacillus subtilis | +++ |
| | +++ |
| Saccharomyces cerevisiae | ++ |
| | ++ |
| Escherichia coli. | +++ |
| | +++ |

Note: +++ represents 10 mm or more growth inhibition zone
++ represents 5-10 mm growth inhibition zone
+ represents 3-5 mm "
± represents 3 mm or less
— represents no growth inhibition zone but mycellium do not grow on the filter (Test with Practical Equipment)

The effect of the antimicrobial agent added-filter net as prepared by the above mentioned procedure was evaluated by measuring the number of microorganisms (bacteria, molds and osmophilic fungi) blown from the blowing port of the air conditioner installed with filter net.

Two air conditioners, one with the antimicrobial agent added-filter net and the other with the filter net without the antimicrobial agent, were normally operated simultaneously in one room.

After operating for the specified period, three culture media were placed on the part of the blowing port of each the air conditioner so as to be exposed to the blown air. After sampling by 10 minutes' operation, the culture media were removed and bacteria were cultivated at 30° C. for three days, molds and osmophilic fungi at 25° C. for seven days. These procedures were performed every day from three days to twenty days after the begining of the operation.

The average numbers of bacteria, molds and osmophilic fungi were as follows.

| | Bacteria | Molds | Osmophilic Fungi |
|---|---|---|---|
| Filter without Antimicrobial agent | 379 (100%) | 28 (100%) | 18 (100%) |
| Antimicrobial agent added Filter | 42 (11.1%) | 16 (57.1%) | 18 (61.1%) |

As shown in the above table, the antimicrobial agent added-filter according to this invention rapidly reduces the number of microorganisms blown from the blowing port.

It was also proved that the antimicrobial effect is maintained for at least 12 months.

We claim:

1. In an air blower apparatus for conditioning a room, said apparatus including a fan, a fan casing, a suction grill, a discharge grill and an air filter, at least one of which is a synthetic resin component which comes in contact with an air flow, the improvement comprising:
at least one synthetic resin component molded from polypropylene resin, to which at least one antimicrobial agent selected from the group consisting of diphenylethers, N-haloalkylthio compounds, benzimidazoles, organic arsine compounds and metal alumino-silicate hydrate is mixed prior to molding of said components.

2. In the air blower apparatus of claim 1 wherein said synthetic resin component comprises an inner layer remote from contact with said air flow and an outer layer for contact with said air flow, only said inner layer containing an antimicrobial agent.

3. In the air blower apparatus of claim 1, wherein said synthetic resin component comprises an inner layer remote from contact with said air flow and an outer layer for contact with said air flow and both said inner and outer layers contain said antimicrobial agent, but said outer layer contains the antimicrobial agent in a lesser cincentration than that of the inner layer.

4. In the air blower apparatus of claim 1 wherein an inclusion compound is formed from said antimicrobial agent prior to mixing with said polypropylene resin.

5. In the air blower apparatus of claim 4 wherein said inclusion compound is formed from said antimicrobial agent with metal alumino-silicate hydrate.

6. In the air blower apparatus of claim 1 wherein said antimicrobial agent is combined with said polypropylene resin by intermediation with a coupling agent.

7. In the air blower apparatus of claim 6, wherein the coupling agent is a silane coupling agent.

8. In the air blower apparatus of claim 6, wherein the coupling agent is a compound having a —CHO radical.

9. The air blower apparatus of claim 6, wherein the antimicrobial agents of a diphenylether and a N-haloalkylthio compound are used in combination.

10. In the blower apparatus of claim 9 in which the diphenylether is 2,4,4'-trichloro-2'-hydroxydiphenylether and the N-haloalkylthio compound is N-(fluorodichloromethylthio)phthalimide.

11. In the air blower apparatus of claim 1 wherein said synthetic resin components is an air filter.

12. In the air blower apparatus of claim 11, wherein the synthetic resin component is a net of an air filter.

13. In the air blower apparatus of claim 1, wherein the concentration of antimicrobial agent ranges from 0.05 wt% to 4.0 wt% of the polypropylene resin as the material of the component.

14. In the air blower apparatus of claim 1, wherein said synthetic resin component is a discharge grill.

15. In the air blower apparatus of claim 1, wherein said synthetic resin component is a suction grill.

16. In the air blower apparatus of claim 1, wherein said synthetic resin component is a fan.

17. In the air blower apparatus of claim 1, wherein said synthetic resin component is a fan casing.

* * * * *